(12) United States Patent
Sasakawa et al.

(10) Patent No.: US 7,094,946 B1
(45) Date of Patent: Aug. 22, 2006

(54) ANIMAL MODEL FOR ALLERGIC DISORDERS

(75) Inventors: Tatsuya Sasakawa, Suita (JP); Yasuyuki Higashi, Izumi (JP); Shozo Sakuma, Nishinomiya (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 09/548,290

(22) Filed: Apr. 12, 2000

(51) Int. Cl.
*A01K 67/00* (2006.01)
*A61K 39/35* (2006.01)
*A61K 38/00* (2006.01)

(52) U.S. Cl. ............................ 800/9; 800/8; 424/275.1; 424/184.1; 424/93.1; 514/2; 530/350; 530/300

(58) Field of Classification Search .................... 800/8; 530/350, 300; 514/2; 424/93.1
See application file for complete search history.

(56) References Cited

OTHER PUBLICATIONS

Yasue et. al.; Inhibition of Airway Inflammation in rDer f 2-Sensitized Mice by Oral Administration of Recombinant Der f 2. 1997. Cellular Immunology 181: 30-37.*

Gad. S. C. 1994. "The mouse ear swelling test (MEST) in the 1990s". Toxicology, vol. 93 (1), 33-46.*

Tsutomu Koizumi et al . . . , "The Role of Immunity on the Development of the Dermatitis in NC Mice", Exp. Anim. vol., 35, No. 2, pp. 159-163, 1986.

Hiroshi Matsuda et al., "Development of Atopic Dermatitis-Like Skin Lesion with IgE Hyperproduction in NC/Nga Mice", International Immunology, vol. 9, No. 3, pp. 461-466, 1996.

Jun Hiroi et al., "Effect of Tacrolimus Hydrate (FK506) Ointment on Spontaneous Dermatitis in NC/Nga Mice", Jpn. J. Pharmacol., vol. 76, pp. 175-183, 1998.

Eishin Morita et al., "Fur Mites Induce Dermatitis Associated with IgE Hyperproduction in an Inbred Strain of Mice, NC/Kuj", Journal of Dermatological Science, vol. 19, pp. 37-43, 1999.

"Guide for the Care and Use of Laboratory Animals", Institute of Laboratory Animal Resources Commission on Life Sciences National Research Council, National Academy Press, Washington, D.C. 1996, pp. 75-76.

* cited by examiner

*Primary Examiner*—Anne M. Wehbe'
(74) *Attorney, Agent, or Firm*—Oblon, Spivak, McClelland, Maier & Neustadt, P.C.

(57) ABSTRACT

An animal suitable as a model for an allergic disorder, wherein the animal is an immuno-modulated animal which has been sensitized with an antigen under a specific pathogen free environment such that when the animal displays allergy symptoms caused by the antigen.

16 Claims, 9 Drawing Sheets

| Day 0 | Day 2 | Day 4 | | Day 7 | Day 9 | Day 11 | | Day 14 | Day 16 | Day 18 |
|---|---|---|---|---|---|---|---|---|---|---|
| ☆ | ☆ | ☆ | | ☆ | ☆ | ☆ | | ☆ | ☆ | ☆ |
| ○ | ○ | ○ | | ○ | ○ | ○ | | ○ | ○ | |
| ◆ | ◆ | ◆ | | ◆ | ◆ | ◆ | | ◆ | ◆ ✱ | |
| ● | ● | ● | | ● | ● | ● | | ● | ● ◀ | |

☆ Thickness of ears measured.
○ Medicines applied three hours before the antigen injection.
◆ The antigen (Dp) injection.
✱ Thickness of ears measured one hour after the antigen injection.
● Medicines applied three hours after the antigen injection.
◀ Thickness of ears measured four hours after the antigen injection.

Figure 9

ANIMAL MODEL FOR ALLERGIC DISORDERS

BACKGROUND OF THE INVENTION

1. Field of the Invention

The present invention relates to an animal suitable as a model for an allergic disorder. The present invention also relates to a method of screening agents for effectiveness in treating the allergic disorder using the inventive animal.

2. Description of the Background

Atopic dermatitis (AD) is known as one of the most common skin diseases among children with personal or a family history of atopy. Patients with AD frequently show elevated IgE levels against many allergens such as mites, pollens and grasses among others, and their prevalence is still increasing. AD is dependent upon not only genetic factors but also environmental factors as well. Epidemiological studies suggest that the onset of AD is influenced by environmental factors including mite antigens and air-pollution as well as mental stress. Mite antigens are especially of interest because of their high potency as allergens. For example, more than 90% patients with AD are positive for IgE-RAST for mite antigens.

Clinical symptoms of AD are improved when mites have been removed. In addition, immunological disturbances have been identified in patients with AD, such as overexpression of IL-4 and IL-5 in the affected skin. Defective IFN-γ production of T cells and IgE hyperproduction of B cells may result from hyperproduction of IL-4.

NC/Nga mice, originated from Japanese fancy mice (Nishiki mouse), were established as an inbred strain in 1955. The NC/Nga strain has some unusual biological characteristics: liver and kidney esterase like a DBA/2 strain, high susceptibility to X-irradiation, and high susceptibility to anaphylactic shock. Some researchers noticed development of spontaneous dermatitis just before or after weaning. For example, it has been shown that NC/Nga mice raised in air-uncontrolled conventional circumstances (conventional NC/Nga mice) spontaneously suffered from AD-like skin lesion with marked elevation in plasma level of total IgE, which was similar to human AD. In contrast, NC/Nga mice grown in a specific pathogen free environment (SPF NC/Nga mice) showed neither clinical sign nor IgE hyperproduction, suggesting the attribution of environmental factors to trigger the skin lesions.

Because multiple environmental factors may be involved in the AD-like inflammation of NC/Nga and because it takes 12–16 weeks for conventional NC/Nga mice to develop severe dermatitis, the conventional NC/Nga mice make it difficult and time consuming to analyze the pathogenesis and thus are not a suitable standard model of AD. Therefore, despite the fact that great attention has been paid to the pathogenesis of AD, the reason why NC/Nga mice suffer from such severe skin lesion only in the conventional conditions is not clearly understood.

Accordingly, it remains an important goal to establish a suitable animal model for more efficient elucidation of the AD pathogenesis, as well as other allergic disorders, and to develop new approaches for treating these disorders.

SUMMARY OF THE INVENTION

It is an object of the present invention to provide an animal which is suitable as a model for an allergic disease.

It is a particular object of the present invention to provide a novel an animal which is suitable as a model for atopic dermatitis.

It is another object of the present invention to provide a method of obtaining the inventive animal.

It is another object of the present invention to provide a method of screening potential treatment agents for an allergic disease by using the animal of the present invention as a model for the disease.

The objects of the present invention, and others, may be accomplished with an animal suitable as a model for an allergic disorder, wherein the animal is an immuno-modulated animal which has been sensitized with an antigen under a specific pathogen free environment such that the animal displays allergy symptoms caused by the antigen.

The objects of the present invention may also be accomplished with a method of producing the animal of the present invention, comprising:

maintaining an immuno-modulated animal in a specific pathogen free environment and sensitizing the animal with the antigen.

The objects of the present invention may also be accomplished with a method of screening for an agent for effectiveness against an allergic disorder, comprising:

applying at least one agent to the animal of the present invention, determining whether the agent reduced the allergy symptom and/or in vitro disorder, correlating a reduction in the allergy symptom and/or in vitro disorder with effectiveness against the allergic disorder, and correlating a lack of reduction in the allergy symptom and/or in vitro disorder with ineffectiveness against the allergic disorder.

Thus, to help researchers understand the pathogenesis of allergic disorders, such as AD, and facilitate their analyses more efficiently, the present invention provides a new animal model with a certain genetic strain in which allergy symptoms are induced by an antigen in well-controlled SPF conditions. The present invention therefore provides an experimental animal which is useful, for example, to examine effect and effectiveness of allergic disorder treatment agents, since measurement of an immunoglobulin level in response to a certain antigen, and histological analyses such as degranuation of mast cells and eosinophil infiltration in atopic dermatitis may be carried out in a short period of time without attribution of environmental factors.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, where.

DETAILED DESCRIPTION OF THE PREFERRED EMBODIMENTS

The preferred embodiments will now be described with reference to the accompanying drawings.

The animal of the present invention is suitable as a model for an allergic disorder, preferable as a model of a human allergic disorder. The animal is an immuno-modulated animal which has been sensitized with an antigen under a specific pathogen free environment (SPF environment) such that when the animal displays allergy symptoms caused by the antigen. Thus, the animal has been maintained under a specific pathogen free environment during which time the animal has been sensitized with the antigen.

The animal of the present invention is produced by maintaining the animal under a specific pathogen free environment. During this time, the animal is sensitized with the antigen. The animal is sensitized with the antigen for as long as necessary to produce allergy symptoms caused by the sensitizing antigen. The term "specific pathogen free environment" is well-recognized by those skilled in the art as referring to conditions in which the animal is not exposed to antigens other than the antigen used for sensitization. In this way, the allergy symptoms produced in the animal are specific for the sensitizing antigen.

In one embodiment, a specific pathogen free environment is set up according to the standard set by Japan Animal Association (See, for example, "SPF Animal: the standard for production and maintenance" 1995, published by Japan SLC, Inc., pages 15–20, the contents of which are incorporated herein by reference).

In one embodiment, the SPF environment is established such that temperature control is set at 23±2° C., humidity control is set at 55±5%. These conditions may be automatically controlled by an air ventilation system. If the temperature falls out of this range or the humidity falls outside the range of 55±10%, an alarm is programmed to sound. Ventilation is performed 15 to 20 times/hour, noise level is kept below 60 dB, light is at 150 to 600 Lx between 7:00 am and 7:00 pm and the air quality level is maintained at class 10,000 according to the NASA standard. A description of a procedure for maintaining such an air quality level is described in Guide for the Care and Use of Laboratory Animals, National Research Council, Institute of Laboratory Animal Resources Commission on the Life Sciences, National Academy Press, Washington, D.C., 1986, incorporated herein by reference in its entirety, at page 76. The biologically permissible range for the temperature is 20–26° C. and 40–70% for the humidity.

Preferably, the animal is a non-human mammal. In this embodiment, the animal may be mouse, rat, guinea pig, rabbit, dog, cat, cow, sheep, or pig. A mouse or a rat is particularly preferred.

As used herein the term "immuno-modulated experimental animal" refers to experimental animal, i.e., an animal customarily used for testing in medical and/or cosmetic research, with some type of immune deficiency or abnormality. Examples of such animals are well-known to those skilled in the art. Examples include an LEC rat, BN/Crj rat, NC/Nga mouse, MRL/1pr mouse, NZW mouse, NBZ mouse, NZW/B F1 mouse. Preferably, it is an experimental animal of a Th 2 kind, because during immune reaction, Th2 (helper T cell 2) dominantly reacts and secretes IL-4, IL-5 and IL-10. In particular, NC/Nga mouse and BN/Crj rat are known as an experimental animal of a Th 2 kind, and are particularly preferred animals in the present invention. A NC/Nga mouse is particularly preferred.

The nature of the antigen is not particularly limited in the present invention, and a wide variety of different types of antigenic materials may be used. Suitable antigens invention include natural compounds, including extracts from natural substances, such as poke weed mitogen, mite, pollens including the pollens from Japanese cedar, dandruff, fur and feather from dogs, cats, mice and rats, among others.

The allergic disorder for which the animal may serve as a model is not particularly limited. Examples of the allergic disorder include atopic dermatitis, atopic asthma, conjunctival allergy, allergic rhinitis, food allergy, urticaria, contact dermatitis, allergic reactions to drugs, and anaphylaxis.

Preferably, the antigen is sensitized by injecting the antigen, a solution and/or suspension thereof, into the skin of the animal. Preferable locations for such injections is the skin of the abdominal cavity or the skin proximal to the ears of the animal. The antigen is preferably injected into the skin on a daily basis until the allergy symptoms appear on the skin surface of the animal. A suitable time period for sensitizing the animal with the antigen is 5 to 50 days. This range includes all specific values and subranges therebetween, such as 8, 10, 15, 20, 25, 30, 35, 40 and 45 days.

The animal of the present invention is particularly useful for method screening an agent for effectiveness against an allergic disorder. In this embodiment, at least one agent is applied the animal at the site of the allergy symptom (topical administration) or administered to the animal orally. Then, it is determined whether the agent reduced the allergy symptom and/or in vitro disorder. If administering the agent causes a reduction in the allergy symptom and/or in vitro disorder, this result is correlated a with effectiveness against the allergic disorder. If the agent does not cause a reduction in the allergy symptom and/or in vitro disorder, this result is correlated with ineffectiveness against the allergic disorder. In a preferred embodiment, multiple agents are screened using this procedure.

Any of the well-known methods can be used to determine whether an agent is effective in reduced the allergy symptom and/or in vitro disorder. Examples of these methods include (a) Measurement of affected areas, particularly measurement of the ventral sides of the ears of the animal, (b) measurement of anti-Dp-specific IgG levels, (c) measurement of cytokine concentration, (d) histological analysis: degranuation of mast cell, (e) histological analysis: eosinophil infiltration in atopic dermatitis (see *J. Invest. Dermatol.* 100, 137, incorporated herein by reference).

This screening method is also useful in evaluating a cytokine production inhibitor. Therefore, once an agent has been identified by this screening method, it may be administered to patients in need thereof. In a preferred embodiment, the patient is a human. Examples of conditions that may be treated using an agent identified in the inventive screening process include organ or tissue allo- or xeno-transplant rejection, e.g., kidney, liver, heart, lung, combined heart-lung, bone marrow, islet cells, pancreatic, skin, chromaffin or dopamine producing cells, small bowel, or corneal transplantation. Treating and/or preventing graft-versus-host disease, such as one which occurs following bone marrow transplantation.

The present invention also provides a method of screening for an agent for effectiveness in preventing an allergic disorder, comprising:

applying at least one agent to the an immuno-modulated experimental animal, sensitizing the animal with an antigen, determining whether the agent prevents an allergy symptom and/or in vitro disorder in the animal, correlating prevention of the allergy symptom and/or in vitro disorder with effectiveness for preventing the allergic disorder, and correlating prevention of the allergy symptom and/or in vitro disorder with ineffectiveness for preventing the allergic disorder.

The ability of an agent to prevent an allergic disorder is determined by whether the agent is effective in preventing symptoms of the allergic disorder. This can be determined by the same methods described for determining whether an agent is effective for reducing the allergy symptom described above.

In the context of the present invention, suitable patients for treatment with the agents identified by the inventive methods include humans and animals. Non-human mammals are the preferred animal patients.

EXAMPLES

Having generally described this invention, a further understanding can be obtained by reference to certain specific examples which are provided herein for purposes of illustration only and are not intended to be limiting unless otherwise specified.

Example 1

Six week old SPF NC/Nga female mice were purchased from Charles River Japan, Inc. or Fujisawa Technical Services Co. Ltd., and kept in SPF condition for more than one week.

Induction of Skin Lesion

10% Nembutal was prepared by diluting Nembutal Injection Fluid, manufactured by Abbott, No. 3778, to 10 parts with saline solution. Mite Antigen was prepared by adjusting Mite Extract-Dp, manufactured by LSL, LG-5449, Lot. 744072, to 2 mg/mL with diluted water and saline solution, and preserved at 20° C. The adjusted mite extract is readjusted to 0.5 mg/mL by using saline solution just before use. The NC/Nga mice were first anesthetized by injecting the 10% Nembutal in the amount of 300 μL/mouse in their abdominal cavities, and then injected with the mite antigen in the amount of 10 μL/ear into the ventral sides of their right ears on the $1^{st}$, $2^{nd}$, $4^{th}$, $6^{th}$, $7^{th}$, $9^{th}$, $11^{th}$, $14^{th}$, $16^{th}$ and $18^{th}$ days of this experiment. Swellings of their right ears were measured by an ear thickness gauge, for example, a peacock dial thickness gauge, 24 hours after each intradermal injection. On the $18^{th}$ day, their bloods were collected and the plasma samples were stored at −20° C. until they were quantitatively analyzed for immunoglobulin.

Statistical Analysis

Data was analyzed for their respective means± s.e. (standard errors). Statistical significances of differences were assessed by Durnnett's multiple comparison. P values of less than 0.05 were considered statistically significant.

Development of AD-Like Skin Lesions

Figure 1:
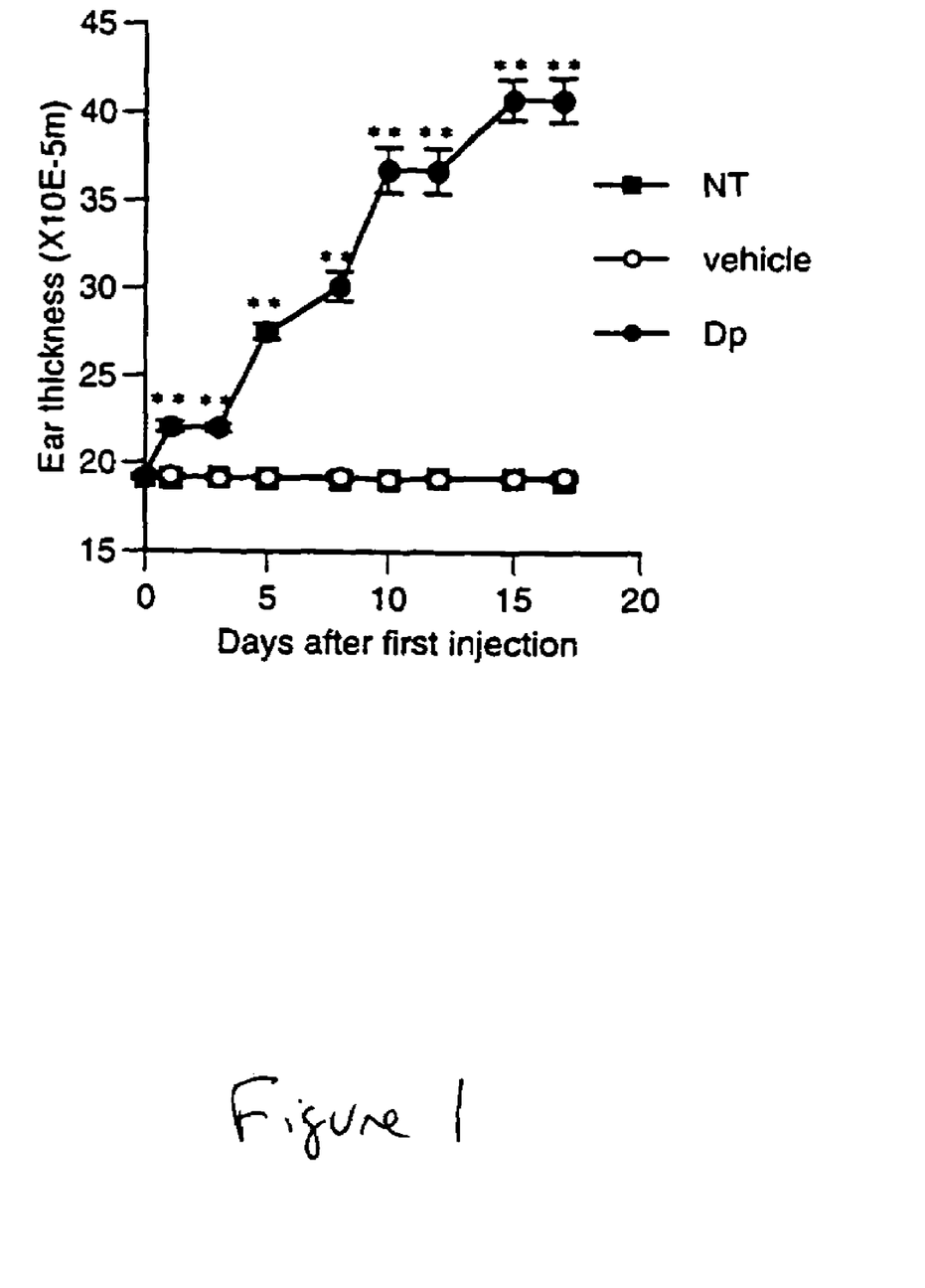
FIG. 1: graph showing swellings of the Dp-injected mice's ears, vehicle, or non-treated after first injection.

FIG. 1 is a graph showing swellings of the mice's ears injected with Dp (●), vehicle (saline solution-injected) (○), or non-treated (■) after first injection. The swellings were measured by using a thickness-gauge 24 hours after each injection. The non-treated mice (NT mice) were measured on the same occasion as the Dp-injected (Dp mice) and vehicle mice were measured. Each point represents the mean± s.e. of ten mice, and p<0.01, when compared with the vehicle group. As seen from FIG. 1, definite swellings were observed in the Dp ears of the mice after 7 days.

FIGS. 2A–B are photographs showing clinical skin features of the right ears of the mice on the $18^{th}$ day. The Dp and NT mice were macroscopically examined 18 days after the first injection. FIG. 2A shows an ear of an NT mouse while FIG. 2B shows an ear of a Dp mouse. Each point represents the means.e. of ten mice.

Figure 2:
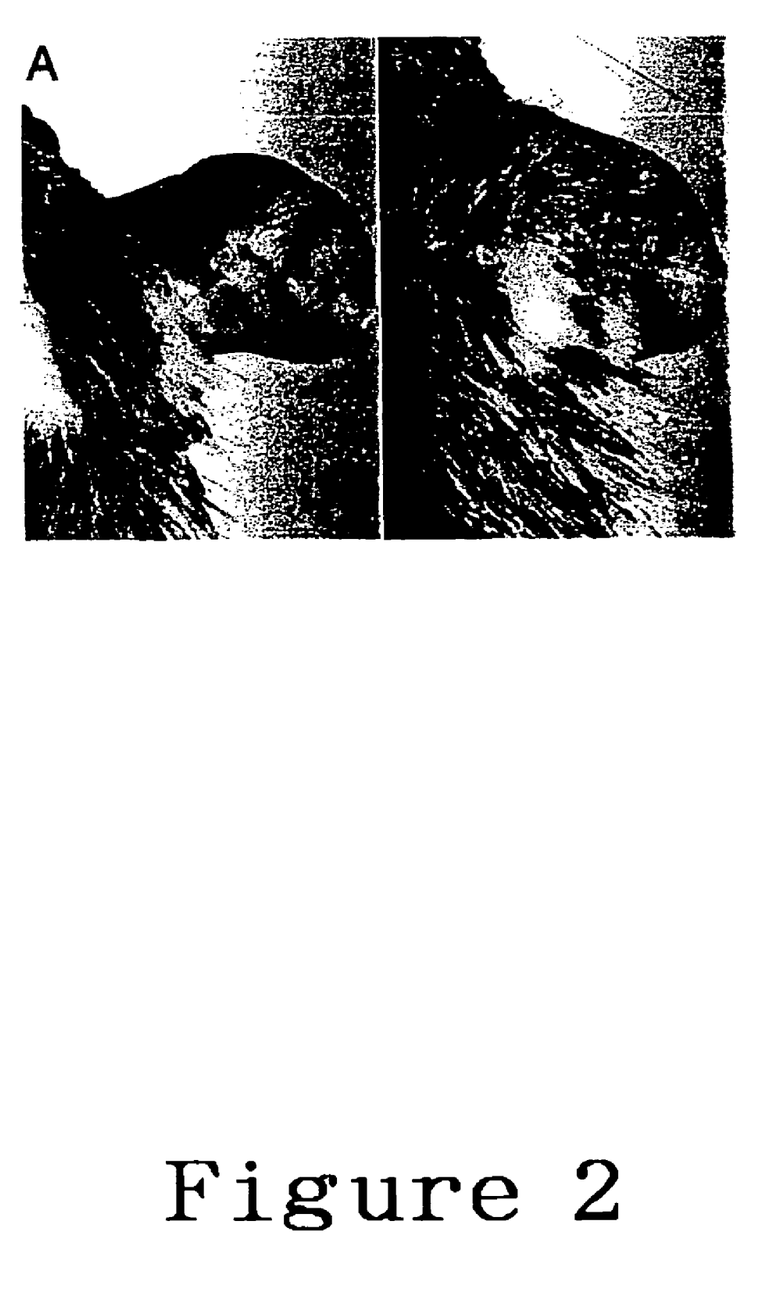
FIGS. 2A–B: photographs showing clinical skin features of mice right ears on the 18th day.

The swellings of the ears became more severe after the $14^{th}$ day after the first Ag injection. The skin lesions such as erythema, edema, excoriation and scaling, typical symptoms in the skin of patients with AD, were observed on the $14^{th}$ day at the dorsal sides of their ears as seen in FIG. 2. On the ventral sides of the injected ears, only erythema were observed (data not shown). Those lesions became more severe on the $18^{th}$ day than those on the $14^{th}$ day. The vehicle mice, i.e., the mice injected only with the saline solution intradermally, showed no skin lesions nor ear swelling as seen in FIG. 1.

1. Histological and Immunohistochemical Analyses

The right ears of the Dp and NT mice were cut to exactly half sections on the $18^{th}$ day from the first injection. Tissues were fixed in 10% phosphate-buffered formalin (pH 7.2), embedded in paraffin, cut at 3 μm, and stained with HE (hematoxylin and eosin) or acidic toluidine blue (pH 4.0). The remaining parts of the ears were embedded in OCT compound (Miles, Inc., Elkhard, Ind.) and snap frozen in dry ice ethanol for immunohistochemistry.

To identify the population of infiltrated cells, HE (hematoxylin and eosin) staining and immumohistochemical stainings, for example, CD4 and F4/80 stainings, were performed. Then, eosinophils and CD4-positive cells, and macrophage were defined. For this immunohistochemical analysis, mAbs for mouse CD4 (PharMingen, San Diego, Calif.) and mAbs for mouse F4/80 (Serotec, Oxford, U.K.) were used.

The frozen sections were cut in 5 μm and fixed in cold acetone. After a treatment of endogenous peroxidase inhibition, anti mouse CD4 or F4/80 were applied overnight. After washing twice, goat anti-rat IgG conjugated with peroxidase (JACKSON, West Grove, Pa.) was overlayed. Visualization was performed with AEC (Aldrich Chemical Company, Milwaukee, Wis.) and counter-stained with mayer's-hematoxylin solution (WAKO).

Figure 3:
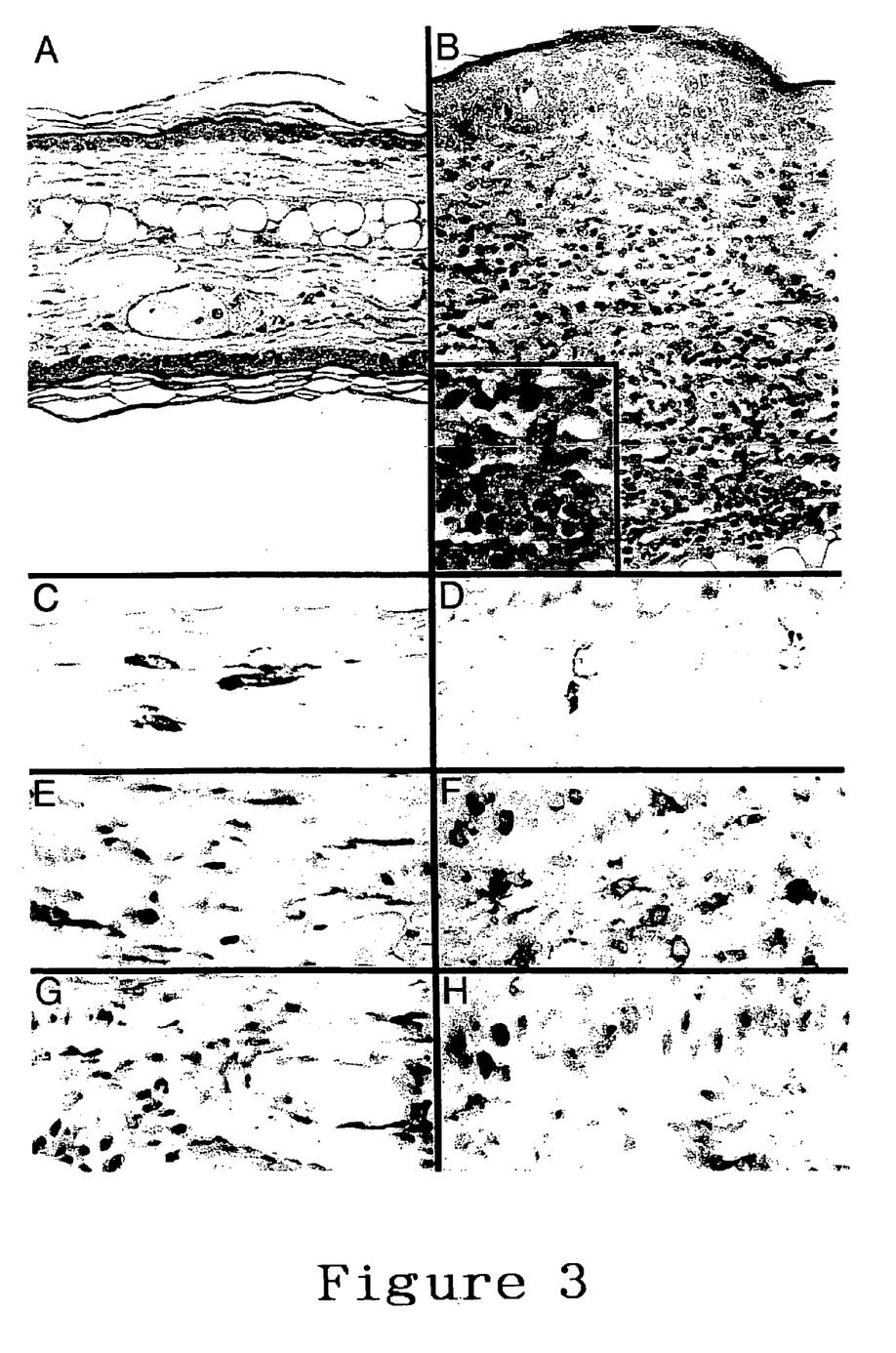
FIGS. 3A–H: photographs showing microscopic histological analysis of the non-treated and Dp-injected mice skins.

FIGS. 3A–H are photographs showing microscopic histological analysis of the NT and Dp mice's skins. FIGS. 3A and 3B show the HE (hematoxylin eosin) staining of the NT and Dp mice's skins on the $18^{th}$ day, respectively. FIGS. 3C and 3D show the toluidine blue staining of the NT and Dp mice's skins, respectively. FIGS. 3E and 3F show the immunostaining for CD4 of the NT and Dp mice's skins, respectively, while FIGS. 3G and 3H show the immunostaining for F4/80 of the NT and Dp mice's skins, respectively.

Referring to FIG. 3B, the histopathological analysis showed that the epidermis was swollen by hyperplasia with areas of parakeratosis in the Dp mice's ears. Severe infiltration of inflammatory cells to dermis was also observed.

FIG. 3D shows that most of the mast cells observed in the Dp mice's skin lesions seem to be degranulated. Infiltration of inflammatory cell and degranulation of mast cells were not observed in the vehicle mice.

2. Cytometric Analysis

Cytokine and Immunoglobulin Production by Lymph Node (LN) Cells

Submandibular lymph nodes of the right ears were collected in sterile condition from the Dp and NT mice on the $18^{th}$ day, and single cell suspensions of the submandibular lymph nodes were made in RPMI 1640 (Life Technologies, Gland Island, N.Y.) supplemented with 10% FCS (Hyclone, Logan, Utah), $10^{-4}$ M 2-ME, 50 U/ml penicillin, and 50 µg/ml streptomycin. The cells in the single cell suspensions were incubated in 24 well-culture plates (Sumitomo Bakelite Co. Ltd., Tokyo, Japan) at a concentration of $5 \times 10^6$ cells/ml with Con A (1 µg/ml WAKO chemical corporation, Osaka, Japan) or IL-6 (100 U/ml PharMingen) at 37° C. under 5% $CO_2$ for 24 hours or 7 days. For immunoglobulin production, the supernatant was collected after 7 days, and for cytokine production, the supernatant was collected after 24 hours.

Measurement of Anti-Dp-Specific IgG Levels by ELISA Method

Anti-Dp-specific IgG levels were measured by an ELISA method using Dp and anti-mouse IgG mAb. 96-well immunoplates (Sumitomo Bakelite Co. Ltd.) were coated with 50 µl of Dp (50 µg/ml) or PBS for negative control and incubated for 1 hours at 37° C. After washing three times and supplemented with 0.05% Tween-20, the plates were blocked with PBS supplemented with 0.5% BSA for 30 minutes at room temperature. After washing, 100 µl of standards and samples were added to the wells and then the plates were incubated for 1 hour at room temperature. After washing, 50 µl of peroxidase-conjugated anti mouse IgG (Zymed, San Francisco, Calif.) was added. After further incubation for 30 minutes at room temperature, the plates were washed and substrate (o-phenylenediamine tablet (Sigma, St. Louis, Mo.) adding $H_2O_2$ as indicated) was added. The absorbance at 492 nm wavelength was measured by SPECTRA MAX 250 (WAKO, Osaka, Japan) after stopping the reaction with $H_2SO_4$.

Total IgE levels were measured by a sandwich ELISA method using two kinds of rat anti-mouse IgE mAb. Immunoplates (Sumitomo Bakelite Co. Ltd.) were coated with 50 µl of mAb to mouse IgE (10 µg/ml, YAMASA, Chiba, Japan) and incubated for 1 hour at 37° C. Plates were washed and blocked. Collected samples or standard mouse IgE (YAMASA) were added to the wells and incubated for 1 hour in room temperature. After washing, 50 µl biotinylated mAb for mouse IgE (YAMASA) was added to the wells and incubated for 1 hour at room temperature. After washing, 200 µl of peroxidase-conjugated streptavidin (Zymed) was added and incubated for 1 hour at 37° C. After washing, o-phenylenediamine was added and the reaction was stopped with $H_2SO_4$. Then, the absorbance at 492 nm wavelength was measured.

Concentration of IL-2, IL-4, IL-5 and IFN-γ in culture supernatant were also measured by a sandwich ELISA method similar to that of total IgE. In these assays, immunoplates were purchased from Nunc (Roskilde, Denmark). As capture Ab, mAbs for mouse IL-2, IL-4, IL-5 and IFN-γ purchased from PharMingen were used. As standard cytokines, rIL-2 (Genzyme TECHNE, Cambridge, Mass.), rIL-4 (TOYOBO, Osaka, Japan), rIL-5 (PharMingen) and rIFN-γ (R&D, Minneapolis, Minn.) were used. As detection Abs, biotin-conjugated mAbs for IL-2, IL-4, IL-5 and IFN-γ were purchased from PharMingen. TMB Peroxidase EIA Kit (Bio Rad Laboratories, Hercules, Calif.) was used as a substrate and the absorbance at 450 nm wavelength was measured after stopping the reaction with $H_2SO_4$.

Ig Production in Plasma by Dp-Ag

Figure 4:
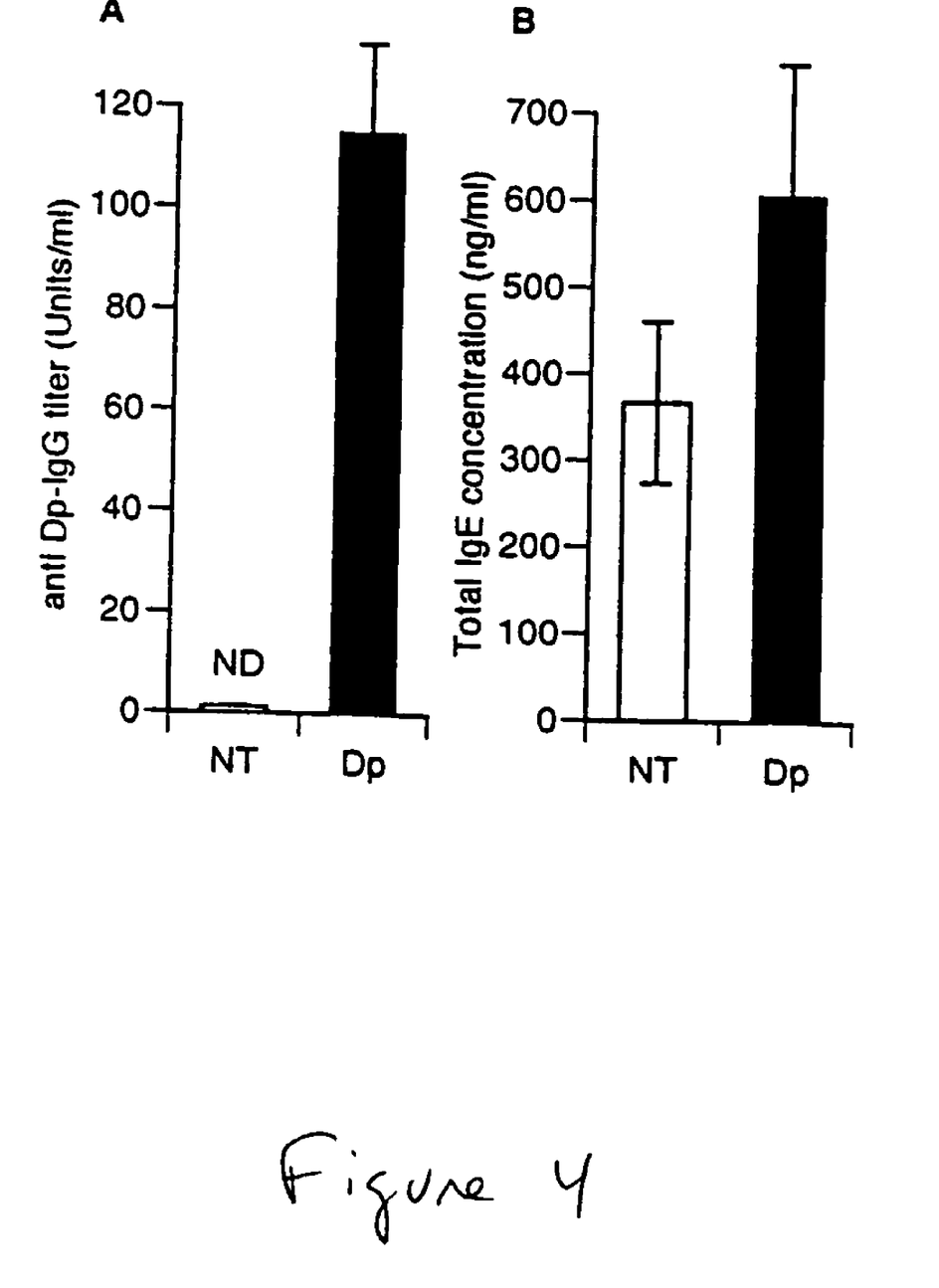
FIGS. 4A–B: graphs showing Dp-specific IgG concentrations and total IgE levels in plasma.

FIGS. 4A–B are graphs showing Dp-specific IgG concentrations and total IgE levels in plasma. Blood was collected on the $18^{th}$ day from retro-orbital plexus and distilled four times with saline solution, and plasma samples were obtained. FIGS. 4A and 4B shows Anti-Dp-specific IgG concentrations and total IgE levels, respectively, as they were measured by the ELISA methods described above. Each point represents the mean±s.e. of seven mice as the measurements were performed in duplicate.

FIG. 4B shows that the total plasma IgE levels in the Dp mice were much higher than those in the NT mice, and FIG. 4A shows that anti-Dp-specific IgG concentrations were elevated in the Dp mice but not in the NT mice.

In Vitro Ig Production by Dp-Ag

To determine which lymphoid tissues were involved in immunoglobulin production caused by the intradermal injection of the Dp-Ag, the immunoglobulin and cytokine production by the LN and splenic cells in vitro were analyzed. Lymph nodes of their right ears and spleens from each group of the mice were collected and homogenated to single cell suspensions.

Figure 5:
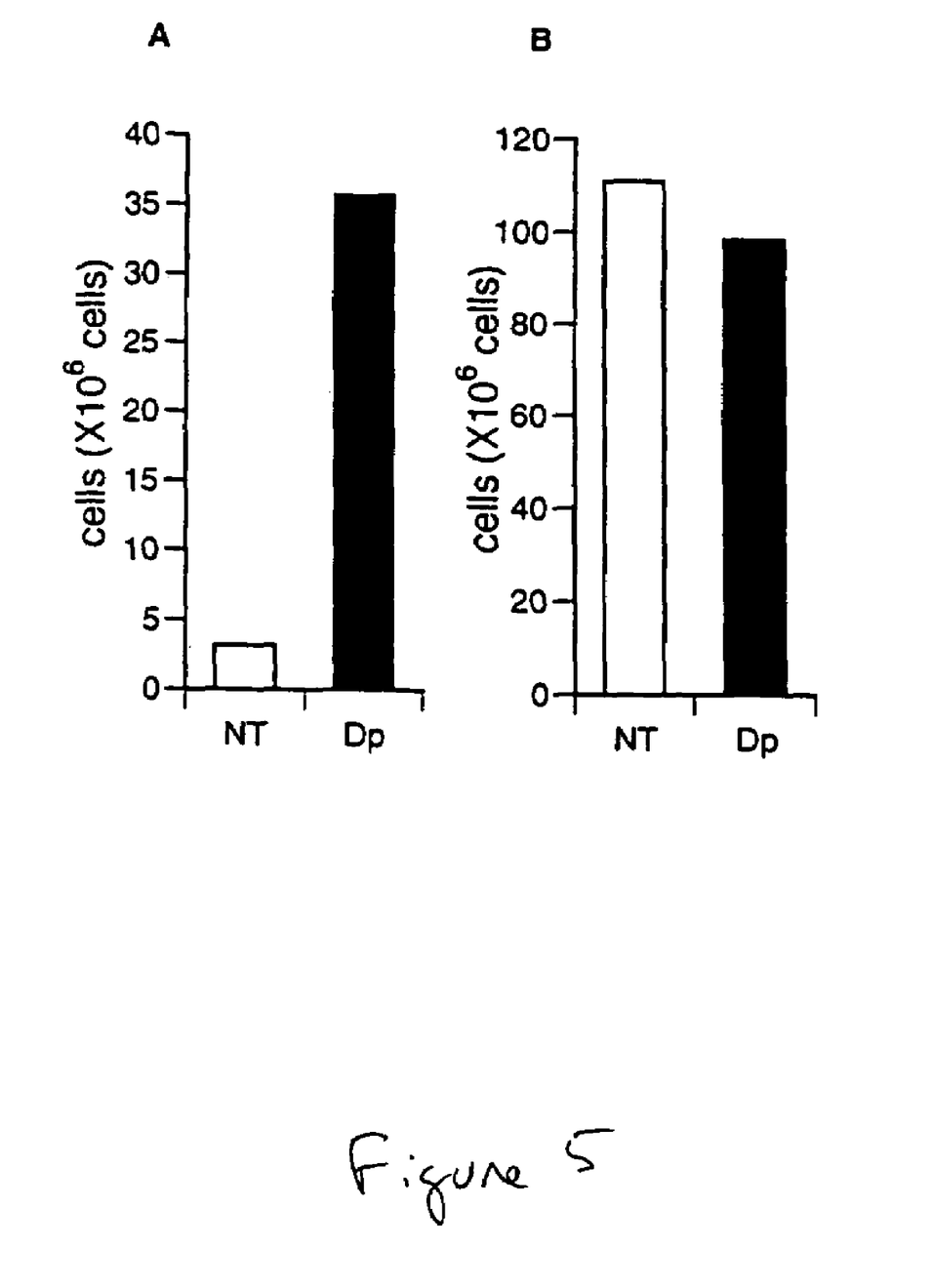
FIGS. 5A–B: graphs showing cell numbers of lymph node cells or spleen cells in the non-treated and Dp-injected mice.

FIGS. 5A–B are graphs showing cell numbers of lymph node cells or spleen cells in the NT and Dp mice. FIGS. 5A and 5B shows cell numbers of the LN cells and the spleen cells, counted with 0.25% trypan-blue solution, respectively. This data was representative in six separate experiments.

At first, number of the LN cells from the Dp mice were dramatically elevated when compared to those of the NT mice as seen from FIG. 5A. However, number of the splenic cells from the Dp mice was not affected, and compatible with those of the NT mice as seen from FIG. 5B.

FIGS. 6A–B are graphs showing in vitro Ig production by the LN cells. The LN cells were incubated $5 \times 10^6$ cells/wells in 24 well culture plates with IL-6 (100 U/ml) or Dp (1 µg/ml). After 7 days, supernatants were collected and Anti-Dp-specific IgG concentrations and total IgE level, as shown in FIGS. 6A and 6B, respectively, were measured by ELISA. This data was representative in six separate experiments performed in duplicate.

Figure 6:
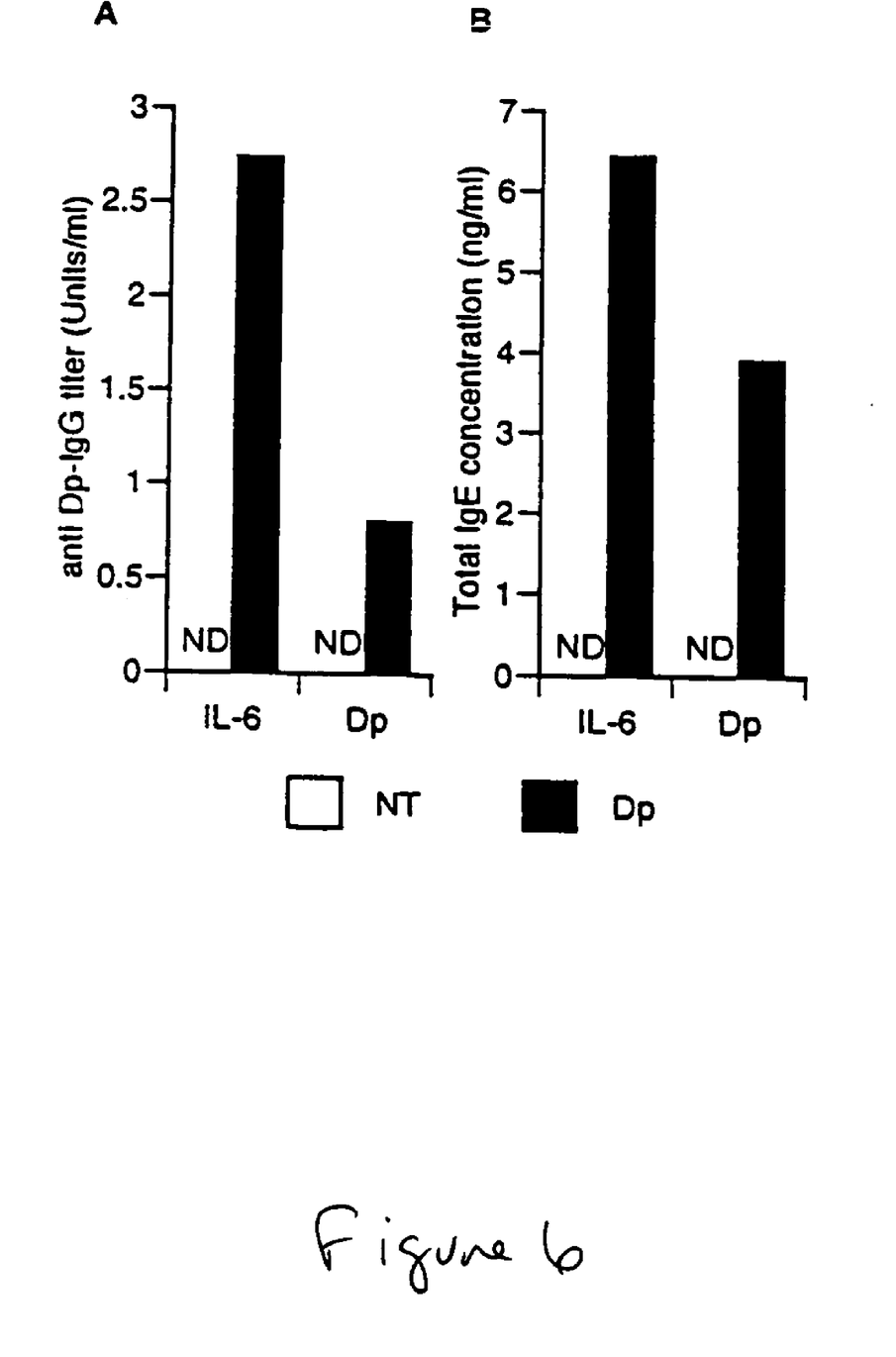
FIGS. 6A–B: graphs showing in vitro Ig production by lymph node cells which were incubated 5×10$^6$ cells/wells in 24 well culture plates with IL-6 (100 U/ml) or Dp (1 μg/ml)

When the LN cells were incubated with the Dp for 7 days, they produced anti-Dp-specific IgG and IgE, suggesting Ag specific Ig production in LN as seen from FIG. 6. The LN cells from the NT mice did not produce immunoglobulins in response to Dp. The splenocytes from neither the Dp nor NT mice produced immunoglobulins (data not shown).

Th2 Responses in Lymph Node (LN) Cells of Dp-Injected Mice

To examine certain cell populations in lymph nodes, flow cytometric analysis was performed by using m-Abs for TCRαβ, CD4, CD8α, CD69, Mac-1 or B220. For flow cytometric analysis, FITC-conjugated mAbs for mouse TCRαβ, CD4, CD8α, CD69, Mac-1, B220 was purchased from PharMingen.

Briefly, single cell suspensions of LN cells were prepared at a concentration of $1 \times 10^6$ cells/ml and stained with those mAbs, and then the LN cell preparations were analyzed by FACScan(Becton Dickinson, Bedford, Mass.). The LN cells were freshly obtained on the $18^{th}$ day. The cells were stained with FITC-conjugated mAbs for mouse TCRαβ, CD4, CD8α, CD69, Mac-1 and B220. The cell preparations were analyzed by a flow cytometer. The percentage of positive cells was calculated from the control. This data was representative in three experiments. Table I shows results from an FACS analysis of the LN cells.

TABLE I

The population in LN cells

| % | NT | Dp |
|---|---|---|
| TCRαβ | 60.95 | 45.53 |
| CD4 | 38.82 | 29.81 |
| CD8α | 18.39 | 15.77 |
| CD69 | 10.73 | 18.21 |
| Mac-1 | 8.83 | 0.77 |
| B220 | 35.28 | 55.16 |

The flow cytometric analysis clearly showed that content of B cells (B220$^+$ cells) and activated T cells (CD69$^+$ cells) were increased as shown in Table 1.

Next, because IL-4 acts as a key cytokine in the process of atopic inflammation, IL-4 synthesis by the LN cells in response to Dp-Ag was investigated.

To examine the populations of IL-4 and/or IFN-γ producing cells in LN, the LN cells were obtained on the 18$^{th}$ day, stimulated with Dp (10 μg/ml) for 19 hours and treated with CytoStain™ Kits (PharMingen) for additional 5 hours. Then, single cell suspensions of the LN cells were prepared at the concentration of 1×10$^6$ cells/ml, and stained with FITC-conjugated mAbs for mouse IFN-γ and with PE-conjugated mAbs for mouse IL-4. IFN-γ and PE-conjugated mAb for mouse IL-4 was purchased from PharMingen as well. After washing, the LN cell preparations were analyzed for flow cytometric analysis by FACScan and the percentage of positive cells was calculated from the control.

Table II shows Th1/Th2 distribution in the LN cells.

TABLE II

Th1/Th2 distribution in LN cells

| % | NT | Dp |
|---|---|---|
| IL-4 (−) IFN-γ (−) | 99.52 | 85.84 |
| IL-4 (+) IFN-γ (−) | 0.23 | 11.52 |
| IL-4 (−) IFN-γ (+) | 0.17 | 0.81 |
| IL-4 (+) IFN-γ (+) | 0.08 | 1.83 |

This data was representative in three experiments. There were detectable Th2 populations, i.e., IL-4 (+) IFN-γ (−) cells, in the LN cells from Dp-injected mice, whereas Th1 population, i.e., IL-4 (−) IFN-γ (+) cells, were not detected.

Figure 7:
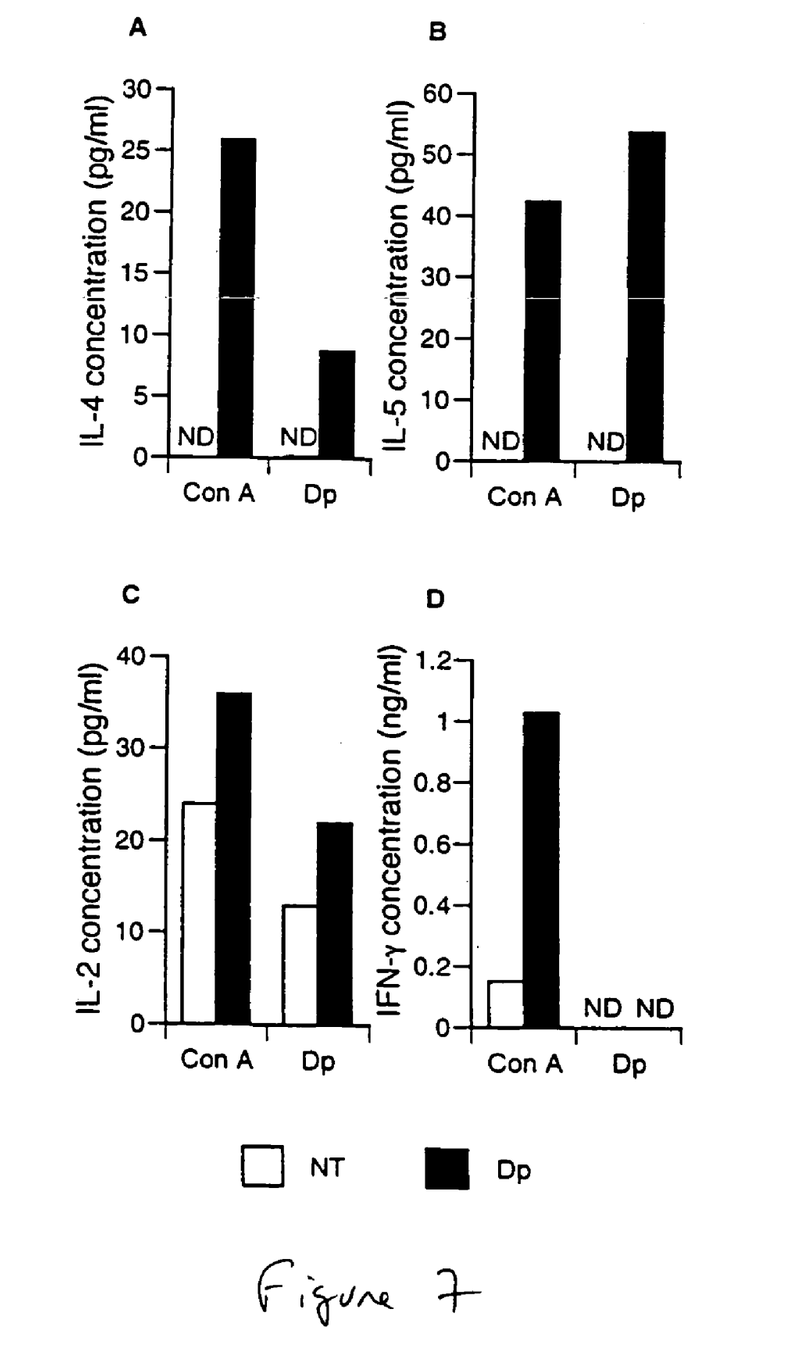
FIGS. 7A–D: graphs showing cytokines production analysis by lymph node cells.

Furthermore, to confirm these Th1/Th2 profiles, the cytokine production of the LN cells by Dp was tested as seen from FIG. 7. The LN cells isolated from the Dp and vehicle mice were stimulated with Con A in the amount of 1 μg/ml or Dp in the amount of 1 μg/ml for 24 hours. Concentration of IL-4, IL-5, IL-2 and IFN-γ were measured from their respective culture supernatants by a ELISA method described above. This data was representative in three separate experiments performed in duplicate.

FIGS. 7A–D are graphs showing cytokines production analysis of the LN cells. Only the LN cells of Dp mice produced IL-4 and IL-5 when stimulated with Ag, but IFN-γ was not detected in the same condition.

AD is thought to be caused by genetic and environmental factors, following skin lesions suffering from degranulation of mast cells and infiltration of inflammatory cells with higher plasma IgE level. Since mite antigen was thought to be a major allergen and induce Th2 response and IgE production in vitro, experiments were conducted for a mite antigen induced model for AD in NC/Nga mice.

As shown above, erythema, edema, excoriation and scaling were observed in the Dp-injected mice. Plasma IgE level was also increased in these experimental model. These symptoms are often observed in the skin lesion of AD patients. Histopathologically, the degranulation of mast cells, epidermal hyperplasia with areas of parakeratosis and infiltration of inflammatory cells to dermis was noticed in the Dp-injected mice's skin lesions. Eosinophils, CD4 positive T cells, and macrophages are remarkably infiltrated into the suffered dermis of the Dp-injected mice. In human AD, it is discussed that the degranulation of mast cells increases skin lesion. Mast cells have high affinity Fc receptor for IgE, and degranulates when Ag is conjugated to IgE on the surface of mast cells. Mast cells secrete many kind of phisiological factors including histamine and LTB4. These factors induce pruritus, which is due to the excoriation, and the main deterioration factor in AD.

Also, skin lesion of human AD and conventional NC/Nga mice were reported to be dramatically recovered with FK506 ointment. FK506 suppresses IL-2 production and proliferation of T cells. Therefore, these data suggest that T cells are very important to initiate and process the skin lesion of AD. FK506 is also reported to suppress the degranulation of mast cells.

In vitro analysis, Anti-Dp-specific IgG and total IgE production by Dp-stimulated LN cells were observed. The LN cells also produced Th2 cytokines of IL-4 and IL-5 with Dp dependent manner. FACScan analysis of LN cells shows that Th2 and B cells are proliferated in response to Dp.

Although conventional NC/Nga animal model show AD like skin lesions with IgE hyperproduction, the conventional circumstances make it difficult to analyze actual cause of the skin lesions. Furthermore, it takes 12–16 weeks for conventional NC/Nga mice to develop severe dermatitis. To elucidate the pathogenesis of AD, and to develop new therapeutic approaches, an NC/Nga model of the present invention is useful to clarify the pathogenesis of human atopic dermatitis and can facilitate its analysis more efficiently, because an NC/Nga model having genetic factors of AD patients according to the present invention develops severe atopic dermatitis induced by the antigen in a short period of time in SPF conditions.

Example 2

Figure 8:
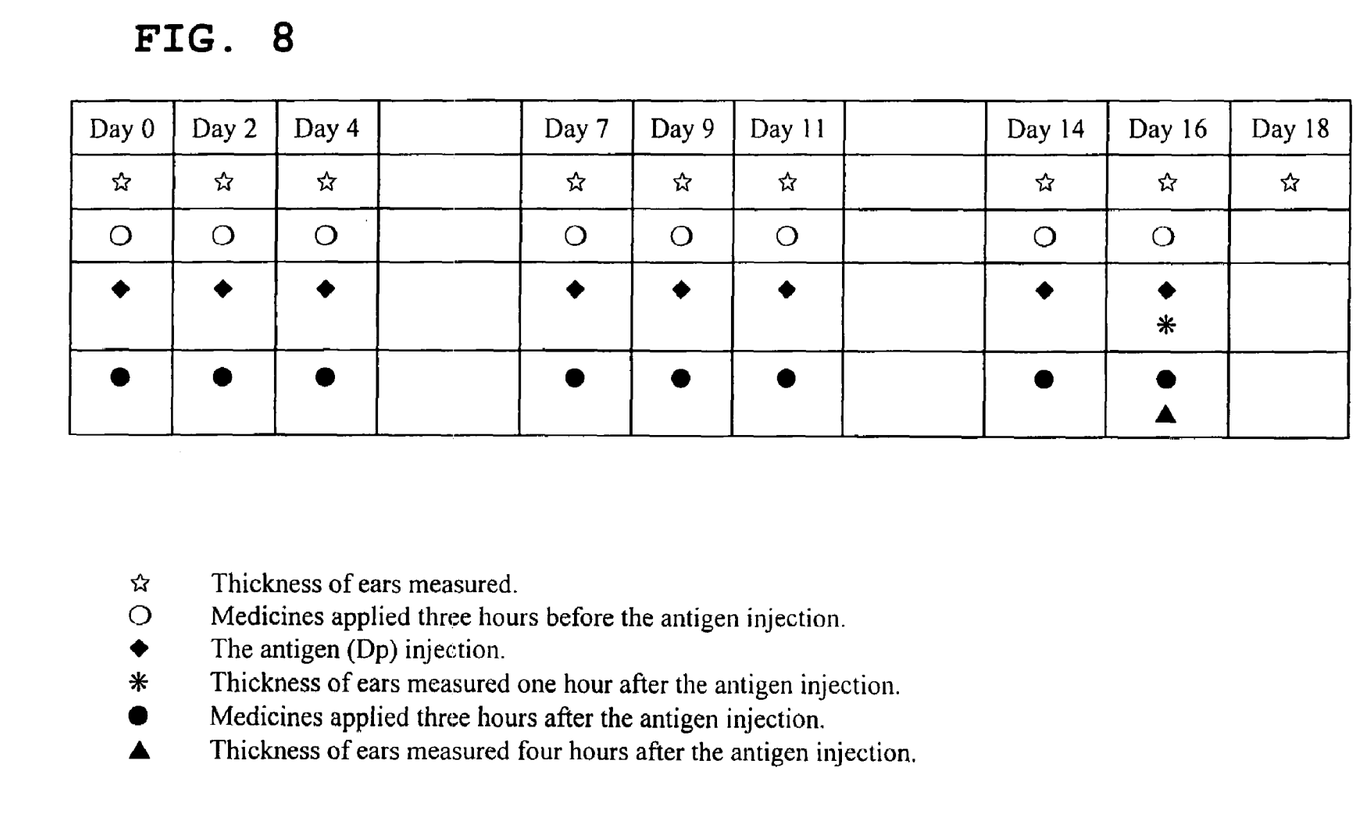
FIG. 8: experimental design of the experiment described in Example 2.

Six week old NC/Nga mice were purchased from Japan Charles River, and used for an experiment when they were seven weeks old. 10% Nembutal was prepared by diluting Nembutal Injection Fluid, manufactured by Abbott, No. 3778, to 10 parts with saline solution. Mite Antigen was prepared by adjusting Mite Extract-Dp, manufactured by LSL, LG-5449, Lot. 744072, to 2 mg/mL with diluted water and saline solution, and preserved at 20° C. The adjusted mite extract is readjusted to 0.5 mg/mL by using saline solution just before use. The NC/Nga mice were first anesthetized by injecting the 10% Nembutal in the amount of 300 μL/mouse in their abdominal cavities, and then injected with the mite antigen in the amount of 10 μ/ear into the ventral sides of their right ears on the 1$^{st}$, 2$^{nd}$, 4$^{th}$, 6$^{th}$, 7$^{th}$, 9$^{th}$, 11$^{th}$, 14$^{th}$, 16$^{th}$ and 18$^{th}$ days of this experiment. The timeline for this experiment is shown in FIG. 8.

The mice were divided into six groups. By using a spatula, atopic dermatitis medicines, namely, 0.03% FK506, 0.1% FK506, 0.3% FK506 and Rinderon (manufactured by Shionogi, Japan), as well as placebo in the amount of 10 μL were plastered onto the ventral sides of the mice's right ears in respective five groups 3 hours before and after the injection of the mite antigen, while one group among the mice remained untreated. Then, by using a peacock dial thickness gauge, swells on the mice's ears in each group were measured from the center of the ear just before the next application of the medicines. In other words, measurements are made 48 hours or 72 hours after each injection. However, on the 16$^{th}$ day of the experiment, measurements are made 1 hour and 4 hours after the injection in the same manner as described above.

Figure 9:
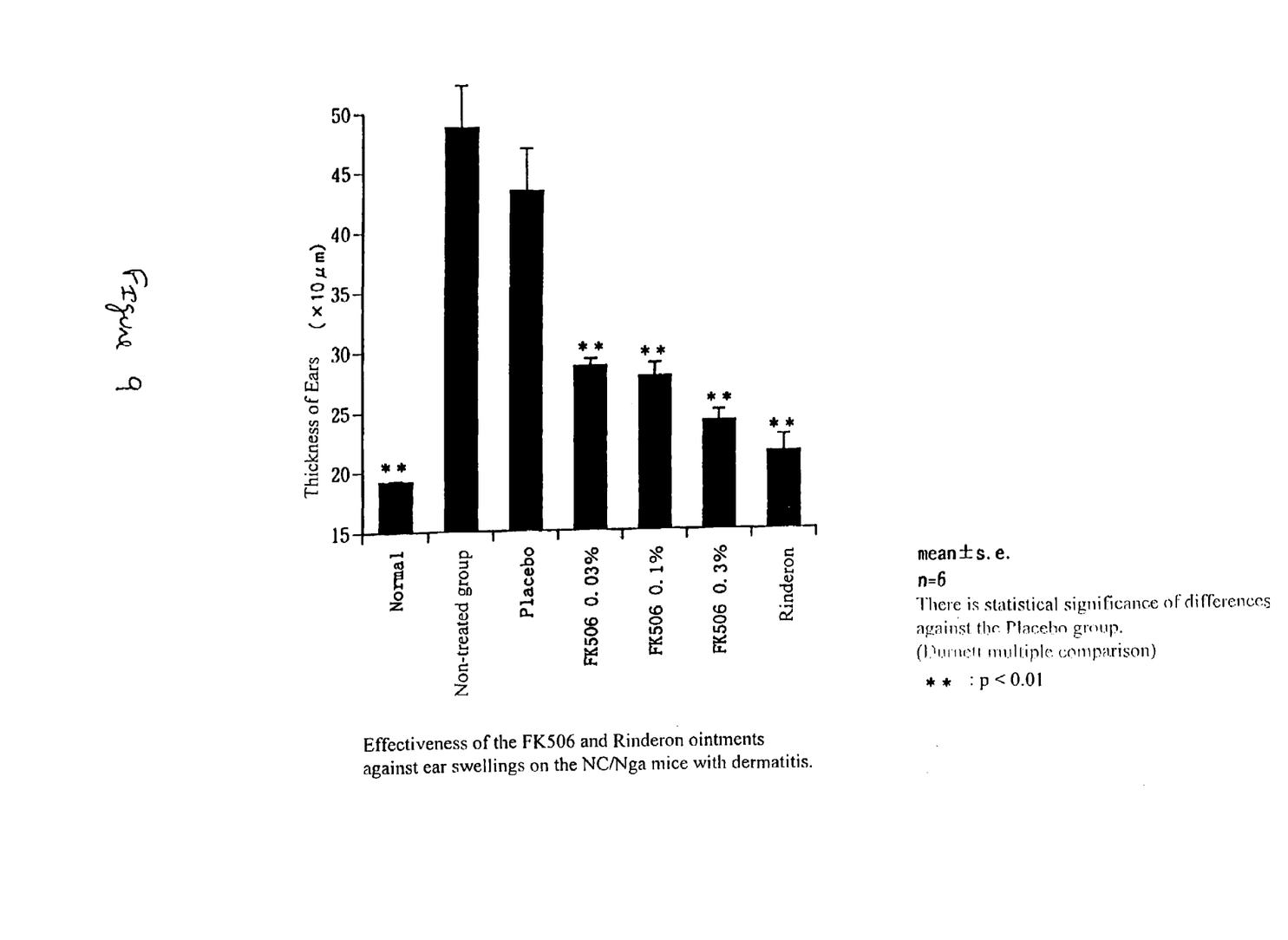
FIG. 9: graph showing the measurements of dermatitis lesions appearing on the mice on the 18$^{th}$ day in the experiment described in Example 2.

FIG. 9 is a graph showing the measurements of dermatitis lesions appearing on the mice on the 18$^{th}$ day. Referring to FIG. 8, the ears of the mice injected with the mite antigen were swollen about 2.5 to 3 times larger in size compared to the ears of the normal mice, showing definite dermatitis lesions on the Dp-injected mice only after eighteen days. Furthermore, among the Dp mice, ones treated with the medicines such as FK506 and Rinderon showed significantly less swelling, indicating the effectiveness of the medicines.

Therefore, within eighteen days, the mice injected with the mite antigen developed dermatitis lesions sufficiently severe for evaluating the effectiveness of these medicines.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. An NC/Nga mouse that has been sensitized with a mite extract by multiple sequential injections of mite antigen over a period 18 days or less in a pathogen-free environment,
   wherein said mouse exhibits at least one symptom of severe dermatitis in a shorter period of time than a conventional NC/Nga mouse; or
   wherein said mouse develops dermatitis lesions sufficiently severe for evaluating the effectiveness of a medicine by day 18.

2. The NC/Nga mouse of claim 1, which exhibits at least one symptom of severe dermatitis in a shorter period of time than conventional NC/Nga mice.

3. The NC/Nga mouse of claim 2, wherein said symptom is a skin lesion on the ear(s) of the mouse.

4. The NC/Nga mouse of claim 1, which develops dermatitis lesions sufficiently severe for evaluating the effectiveness of a medicine by day 18.

5. The NC/Nga mouse of claim 1, which develops skin lesions characterized by erythema, edema, excoriation, and/or scaling.

6. The NC/Nga mouse of claim 1, which develops skin lesions characterized by erythema.

7. The NC/Nga mouse of claim 1, which develops skin lesions characterized by ear swelling.

8. A method of producing the NC/Nga mouse of claim 1, comprising:
   maintaining a NC/Nga mouse in a specific pathogen free environment and sensitizing the ear(s) of the mouse with the mite extract.

9. A method of producing the NC/Nga mouse of claim 1, comprising:
   maintaining a NC/Nga mouse in a specific pathogen free environment and sensitizing the ear(s) of the mouse with the mite extract by multiple sequential injections of mite antigen over a period of 18 days or less in a pathogen-free environment.

10. A method of screening for an agent for effectiveness against atopic dermatitis, comprising:
    applying at least one agent to the mouse of claim 1,
    determining whether the agent reduces one or more symptoms of atopic dermatitis,
    correlating a reduction in said one or more symptoms with effectiveness of said agent against atopic dermatitis, or
    correlating a lack of reduction in said one or more symptoms with ineffectiveness of said agent against atopic dermatitis.

11. The method of claim 10, wherein said determining comprises measuring the affected areas of the mouse.

12. The method of claim 10, wherein said determining comprises measuring the affected areas at the ventral sides of the ears of the mouse.

13. The method of claim 10, wherein said determining comprises measuring anti-Dp-specific IgG levels in said mouse.

14. The method of claim 10, wherein said determining comprises measuring the concentration of at least one cytokine in said mouse.

15. The method of claim 10, wherein said determining comprises measuring degranulation of mast cells in said mouse.

16. The method of claim 10, wherein said determining comprises measuring eosinophil infiltration in said mouse.

* * * * *